United States Patent
Al-Ali

(10) Patent No.: US 8,652,060 B2
(45) Date of Patent: Feb. 18, 2014

(54) PERFUSION TREND INDICATOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 1641 days.

(21) Appl. No.: 12/011,011

(22) Filed: Jan. 22, 2008

(65) Prior Publication Data

US 2008/0221464 A1 Sep. 11, 2008

Related U.S. Application Data

(60) Provisional application No. 60/881,656, filed on Jan. 20, 2007.

(51) Int. Cl.
*A61B 5/02* (2006.01)

(52) U.S. Cl.
USPC .......................................... 600/500; 600/501

(58) Field of Classification Search
None
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |

(Continued)

*Primary Examiner* — Benjamin P Blumel
(74) *Attorney, Agent, or Firm* — Knobbe Martens Olson & Bear LLP

(57) ABSTRACT

A perfusion trend indicator inputs a plethysmograph waveform having pulses corresponding to pulsatile blood flow within a tissue site. Perfusion values are derived corresponding to the pulses. Time windows are defined corresponding to the perfusion values. Representative perfusion values are defined corresponding to the time windows. A perfusion trend is calculated according to differences between representative perfusion values of adjacent ones of the time windows.

12 Claims, 6 Drawing Sheets

(56) References Cited

U.S. PATENT DOCUMENTS

| | | |
|---|---|---|
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 2006/0220881 A1* | 10/2006 | Al-Ali et al. ............... 340/573.1 |

* cited by examiner

PERFUSION TREND INDICATOR

CROSS-REFERENCE TO RELATED APPLICATIONS

This application claims priority from U.S. Provisional Patent Application No. 60/881,656 filed Jan. 20, 2007, titled Perfusion Index Trend Indicator and incorporated by reference herein.

BACKGROUND OF THE INVENTION

Pulse oximetry is a widely accepted noninvasive procedure for measuring the oxygen saturation level of arterial blood, an important physiological measurement in, for example, critical care and surgical applications. A pulse oximeter typically provides a numerical readout of the patient's oxygen saturation and pulse rate. In addition, a pulse oximeter may display the patient's plethysmograph waveform, which is a visualization of blood volume change over time due to pulsatile arterial blood flow.

Pulse oximetry utilizes a noninvasive sensor to measure oxygen saturation ($SpO_2$) and pulse rate of a person. The sensor has light emitting diodes (LEDs) that transmit optical radiation of red and infrared wavelengths into a tissue site and a detector that responds to the intensity of the optical radiation after attenuation by pulsatile arterial blood flowing within the tissue site. Such reading through motion oximeters have gained rapid acceptance in a wide variety of medical applications, including surgical wards, intensive care and neonatal units, general wards, home care, physical training, and virtually all type of monitoring scenarios.

Pulse oximeters capable of reading through motion induced noise are disclosed in at least U.S. Pat. Nos. 6,770,028, 6,658,276, 6,584,336, 6,263,222, 6,157,850, 5,769,785, and 5,632,272, which are assigned to Masimo Corporation ("Masimo") of Irvine, Calif. and are incorporated by reference herein. Low noise pulse oximetry sensors are disclosed in one or more of U.S. Pat. Nos. 7,027,849, 6,985,764, 6,934,570 6,760,607 6,377,829 6,285,896 5,782,757 5,638,818, which are also assigned to Masimo and incorporated by reference herein. Moreover, pulse oximeters capable of reading through motion induced noise and low noise optical sensors including LNOP® disposable, reusable and/or multi-site sensors and Radical®, Rad-5™, Rad-8™, Rad-9™, PPO+™ monitors are also available from Masimo.

Multiple parameter monitors and multiple wavelength sensors are described in U.S. patent application Ser. No. 11/367,033 entitled Noninvasive Multiple Parameter Patient Monitor filed Mar. 1, 2006 and U.S. patent application Ser. No. 11/367,013 entitled Multiple Wavelength Sensor Emitters filed Mar. 1, 2006, incorporated by reference herein. Moreover, multiple parameter monitors and multiple wavelength sensors including Rad-57™ and Radical-7™ monitors and Rainbow™ Rainbow™-brand adhesive and reusable sensors are available from Masimo. MS-brand processor boards incorporating SHARC® DSPs from Analog Devices, Inc. are also available from Masimo.

SUMMARY OF THE INVENTION

A perfusion index trend indicator advantageously provides a mechanism to alert clinicians to important changes in PI compared to a patient's baseline PI. In an embodiment, a PI baseline is established and a PI trend is derived. A user-selectable alarm allows a clinician to request an audible and visual alert if PI trend at a monitored tissue site decreases by more than a specified amount $\Delta PI$ from the PI baseline over a specified time interval $\Delta T$. Both $\Delta PI$ and $\Delta T$ are selectable by the user within established ranges.

One aspect of a perfusion trend indicator comprises inputting a plethysmograph waveform, deriving perfusion values, defining time windows, determining representative perfusion values and calculating a perfusion trend. The plethysmograph waveform has pulses corresponding to pulsatile blood flow within a tissue site. The perfusion values correspond to the pulses. The time windows correspond to the perfusion values. The representative perfusion values correspond to the time windows. The perfusion trend is calculated according to differences between the representative perfusion values of adjacent ones of the time windows.

In various embodiments, the representative perfusion values are determined by trimming the perfusion values within each of the time windows and calculating a mean perfusion value for each of the time windows according to the trimmed perfusion values. The trimming comprises sorting the perfusion values within each of the time windows from the largest of the perfusion values to the smallest of the perfusion values and deleting at least one of the largest perfusion values and at least one of the smallest perfusion values from each of the time windows. Deriving perfusion values comprises identifying peaks and valleys for the pulses, calculating AC values for the pulses from the peaks and the valleys, calculating DC values for the pulses and normalizing the AC values with the DC values. Inputting comprises using an IR channel for the plethysmograph waveform, physiologically acceptable pulses of the plethysmograph waveform are identified using a red channel.

Another aspect of a perfusion trend indicator comprises an optical sensor that transmits multiple wavelengths of optical radiation into a tissue site, detects the optical radiation after attenuation by pulsatile blood flowing within the tissue site, and generates a sensor signal responsive to the detected optical radiation. A patient monitor demodulates the sensor signal so as to generate plethysmograph channels. A digital signal processor (DSP) within the patient monitor inputs at least one of the plethysmograph channels and outputs a perfusion parameter accordingly. A perfusion process executes on the DSP so as to derive a perfusion trend from at least one of the plethysmograph channels. A patient monitor output is responsive to the perfusion trend.

In various embodiments the perfusion process comprises a plethysmograph input corresponding to the at least one plethysmograph channel having pleth features and a measure pleth process that extracts perfusion values from the plethysmograph according to the pleth features. The perfusion process further comprises a perfusion trend calculation that generates trend values from the perfusion values. The perfusion process further comprises a trim process that deletes outlying ones of the perfusion values within a time window according to predetermined criterion. The patient monitor output generates a perfusion trend graph of the trend values versus time. The perfusion trend graph pops-up in a patient monitor display when the trend values after a predetermined time $\Delta T$ are less than a predetermined change in the perfusion index $\Delta PI$. The trend values are each responsive to a median of perfusion index (PI) values.

A further aspect of a perfusion trend indicator has a sensor that transmits multiple wavelengths of optical radiation into a tissue site and that detects the optical radiation after attenuation by pulsatile blood flow within a tissue site so as to provide a plethysmograph input to a digital signal processor (DSP). The input is selected from channels corresponding to the multiple wavelengths. The DSP executes instructions for deriving perfusion index values from the plethysmograph. The perfusion trend indicator comprises a plethysmograph input, a measuring means for generating perfusion index (PI) values from the plethysmograph input according to predefined plethysmograph features and a calculation means for deriving PI trend values from the PI values. In various embodiments, the perfusion trend indicator further comprises a window means for identifying groups of PI values, a trimming means for deleting outlying values from each of the identified PI value groups, a median means for deriving PI trend values from the trimmed PI values, a summing means for determining a PI trend from the PI trend values and a pop-up means for displaying the PI trend when the PI trend is less than a predetermined perfusion index $\Delta PI$ after a predetermined time $\Delta T$.

DETAILED DESCRIPTION OF THE PREFERRED EMBODIMENTS

Figure 1:
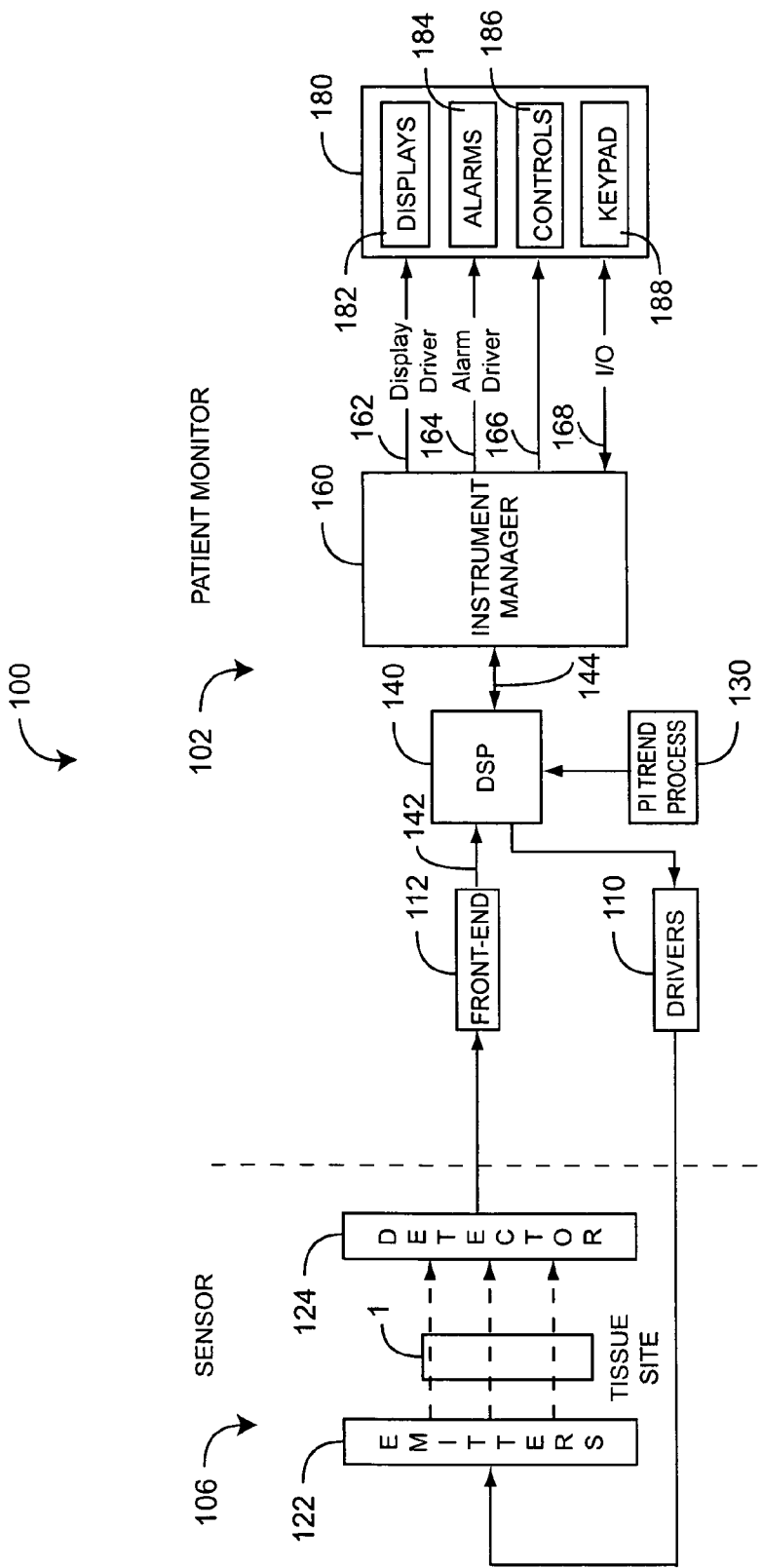
FIG. 1 is a general block diagram of a perfusion trend system.

FIG. 1 illustrates a perfusion trend system 100 embodiment, which measures perfusion, calculates and displays perfusion trends and alerts caregivers to significant changes in a patient's perfusion. The perfusion trend system 100 advantageously provides at least some of displays, alarms or controls responsive to perfusion trend so as to indicate, and affect the treatment of, a patient condition. The perfusion trend system 100 may further generate $SpO_2$, pulse rate (PR), perfusion index (PI), signal quality and in multiple wavelength configurations additional blood parameter measurements such as HbCO and HbMet.

As shown in FIG. 1, the perfusion trend system 100 has a patient monitor 102 and a sensor 106. The sensor 106 attaches to a tissue site 1 and includes a plurality of emitters 122 capable of irradiating the tissue site 1 with at least two wavelengths of light, such as the red and infrared (IR) wavelengths utilized in pulse oximeters and in some configurations multiple wavelengths different than or in addition to those red and IR wavelengths. The sensor 106 also includes one or more detectors 124 capable of detecting the light after attenuation by the tissue 1.

Also shown in FIG. 1, the patient monitor 102 communicates with the sensor 106 to receive one or more intensity signals indicative of one or more physiological parameters and displays the parameter values. Drivers 110 convert digital control signals into analog drive signals capable of driving sensor emitters 122. A front-end 112 converts composite analog intensity signal(s) from light sensitive detector(s) 124 into digital data 142 input to the DSP 140. The input digital data 142 is referred to herein as a plethysmograph waveform, plethysmograph or pleth for short. The digital data 142 has plethysmograph channels corresponding to each emitter wavelength, such as a red channel and an IR channel. The digital data 142 is representative of a change in the absorption of particular wavelengths of light as a function of the changes in body tissue resulting from pulsing blood. The DSP 140 may comprise a wide variety of data and/or signal processors capable of executing programs for determining physiological parameters from input data. In an embodiment, the DSP executes one or more perfusion trend processes 130, such as described with respect to FIGS. 3-6, below. In an embodiment, the perfusion trend processes 130 may be implemented in software, firmware or other form of code or instructions, or logic or other hardware, or a combination of the above.

Further shown in FIG. 1, the instrument manager 160 may comprise one or more microcontrollers controlling system management, such as monitoring the activity of the DSP 140. One or more output devices 180 include displays 182, alarms 184 and controls 186. Displays 182 may be numerical, such as readouts, or graphical, such as trends and bar graphs, generated by LEDs, LCDs or CRTs to name a few. Displays 182 may also be indicators, such as LEDs of various colors that signify variability magnitude. Alarms 184 may be visual or audible indications that variability is, say, above a predetermined threshold. Controls 186 may be inputs to medical equipment, such as drug administration devices, ventilators and fluid IVs, so as to control the amount of administered drugs, ventilator settings or the amount of infused fluids based up pleth variability. The instrument manager 160 also has an input/output (I/O) port 168 that provides a user and/or device interface for communicating with the monitor 102. User input devices 188 may include a keypad, touch screen, pointing device, voice recognition device, network and computer, to name a few. In an embodiment, the I/O port 168 provides initialization settings for PV processes, as described below. The monitor 102 may also be capable of storing or displaying historical or trending data related to PV and other measured parameters or combinations of measured parameters.

Figure 2:
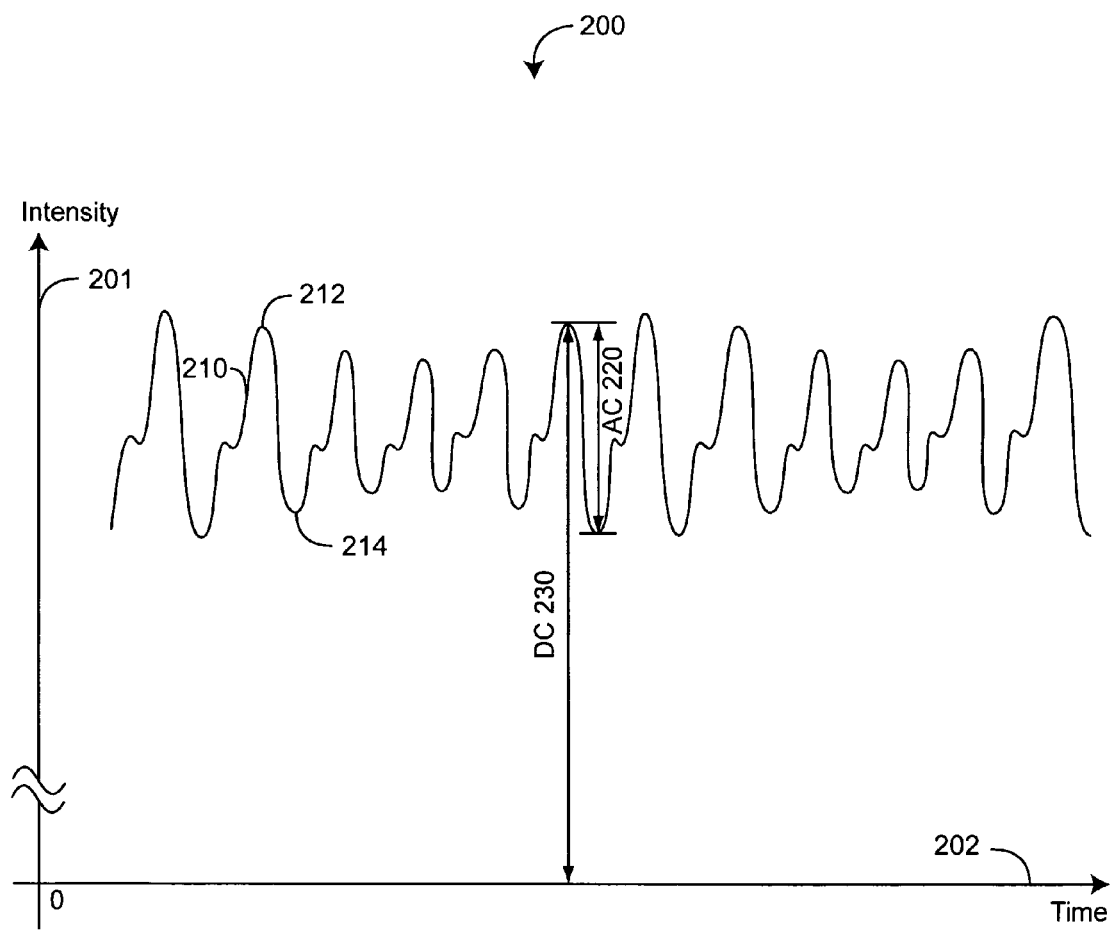
FIG. 2 is a graph of an exemplar plethysmograph.

FIG. 2 illustrates a plethysmograph 200 plotted on an intensity axis 201 versus a time axis 202. The plethysmograph 200 has multiple pulses 210 each with a peak 212 and a valley 214 and extending over a time period 216. A perfusion index (PI) value can be defined for each pulse 210:

$$PI = \frac{AC}{DC} \qquad (1)$$

"AC" 220 designates a peak amplitude 212 minus a valley amplitude 214 for a particular pulse. "DC" 230 designates a peak amplitude 212 for a particular pulse. Perfusion Index (PI) provides a measure of blood perfusion at a sensor site and is useful as a wellness indicator, an indicator of painful stimuli and as a predictor of a deteriorating patient condition. In an embodiment, PI is calculated as a percentage ratio of the AC and DC components of the IR sensor signal, corresponding to pulsatile and non-pulsatile blood volume, respectively. In another embodiment, PI is calculated in similar fashion from the red sensor signal.

Figure 3:
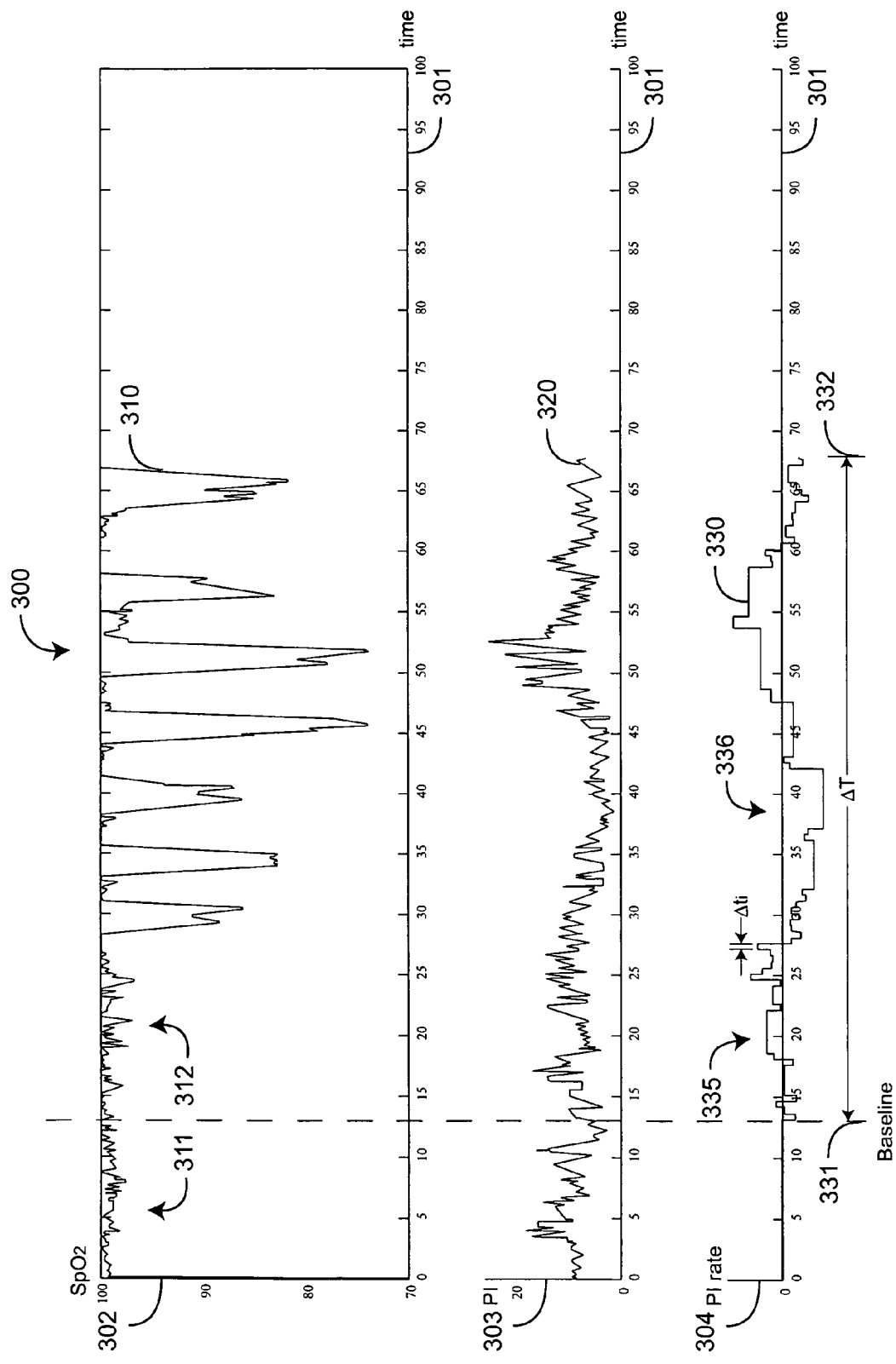
FIG. 3 is a timing diagram chart for a perfusion trend indicator.

FIG. 3 illustrates graphs 300 of oxygen saturation ($SpO_2$), PI and PI rate, each having a common time axis 301 and corresponding $SpO_2$ 302, PI 303 and PI rate 304 axes. The $SpO_2$ graph 310 illustrates an unstable data portion 311 and a stable data portion 312. Unstable data may be due to, for example, poor signal quality, plethysmograph waveform distortion and noise, as described in U.S. Pat. No. 6,606,511 entitled Pulse Oximetry Pulse Indicator, which is assigned to Masimo and incorporated by reference herein. The PI graph 320 illustrates calculated PI values. The PI rate graph 330 illustrates PI rate, as described in detail below. In particular, PI rate 330 begins at zero from a baseline time 331 and continues until a new baseline is set. In an embodiment, a baseline is set at the beginning of a stable data portion 312. PI rate 330 provides a single value for each of multiple adjacent time windows $\Delta t_i$, such as every half-minute, as shown. Positive PI rate values 335 indicate periods when PI is trending overall upwards as compared to the PI baseline. Negative PI rate values 336 indicate periods when PI is trending overall downwards as compared to the PI baseline. A calculated PI trend value indicates the PI rate at the end of a predetermined time interval $\Delta T$ 332 from the baseline, as described below.

Figure 4:
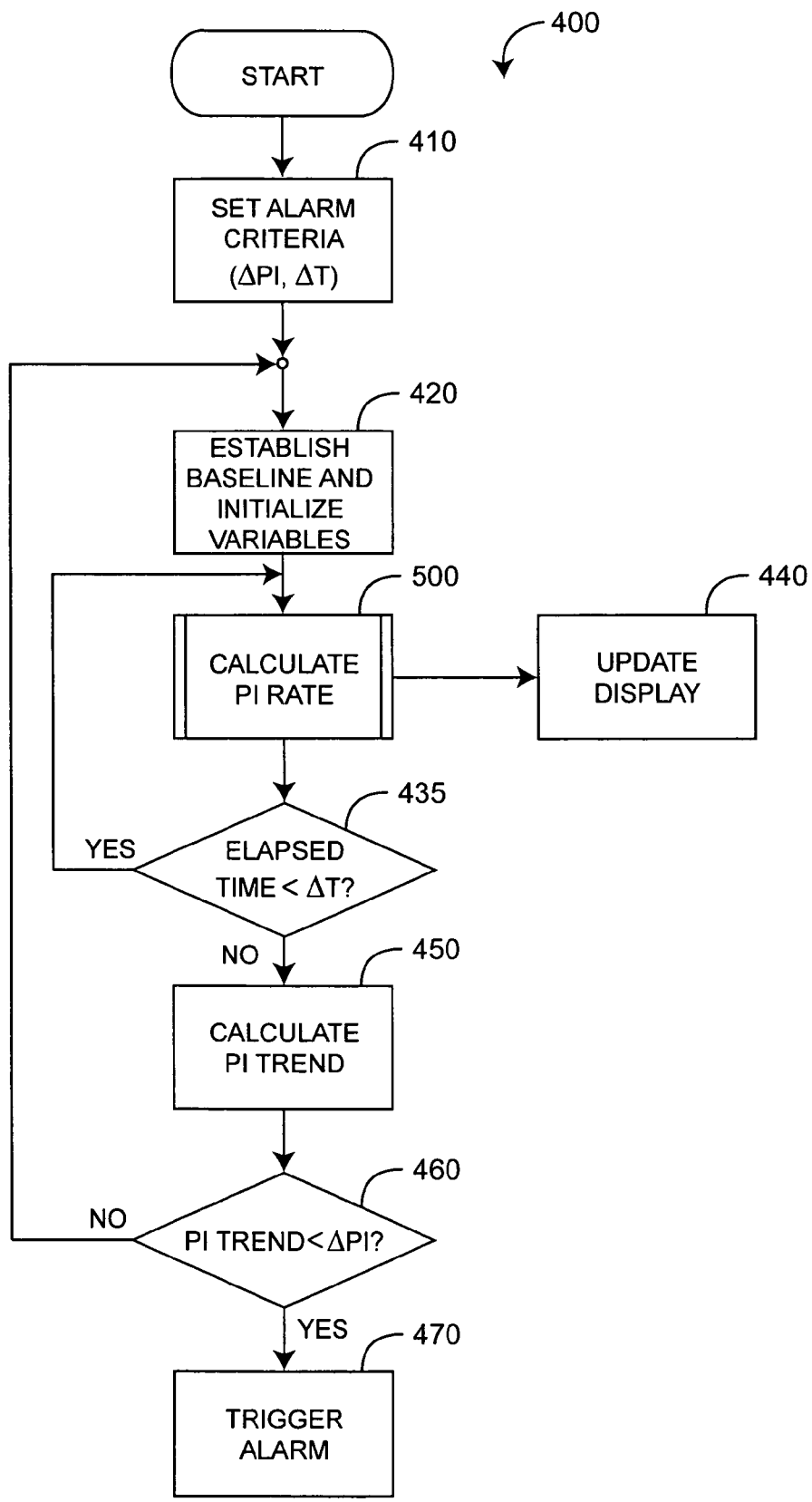
FIG. 4 is a flowchart for a perfusion trend indicator.

FIG. 4 illustrates a perfusion trend indicator 400. Alarm criteria are set 410. In an embodiment, these criteria include a PI interval, $\Delta PI$, over a time interval, $\Delta T$. PI is a percentage ratio, as described above, and an alarm occurs on a sufficiently steep downward PI trend. Hence, the preset $\Delta PI$ criterion is a negative number expressed as a percentage. In a particular embodiment, $\Delta PI$ is set in a range of −1% to −5% in 0.1% increments, with a default of −1%. In a particular embodiment, $\Delta T$ is set in a range of 5 min. to 1 hr. in 5 min. increments, with a default of 15 min.

Also shown in FIG. 4, a baseline 331 (FIG. 3) is established 420 from which to measure the alarm criteria. Various parameters are initialized accordingly, including an integer index, i, a PI rate and an elapsed time, all set to zero. These parameter are described with respect to FIG. 5, below. In an embodiment, a baseline can be manually set, such as based upon visual inspection of a displayed plethysmograph, or automatically set by the system on a stable signal 312 (FIG. 3). A stable pulse oximetry sensor signal is described in U.S. Pat. No. 6,606,511, cited above. If the signal is not stable, the system waits to detect a stable signal. Once a baseline PI is established 420, a PI rate is calculated 500, as described in detail with respect to FIG. 5, below. The elapsed time from the baseline is then determined 435. If the elapsed time is less than the specified $\Delta T$, then calculations of PI rate continue 500. If the elapsed time equals or exceeds $\Delta T$ 435, then PI trend is calculated 450. The PI trend is compared to the specified $\Delta PI$ 260. If the PI trend is not less than $\Delta PI$, then PI has either increased, remained stable or at least not decreased at a sufficient rate to warrant an alarm, and a new baseline is established 420. If the PI trend is less than $\Delta PI$ 460 an alarm is triggered 470.

Figure 5:
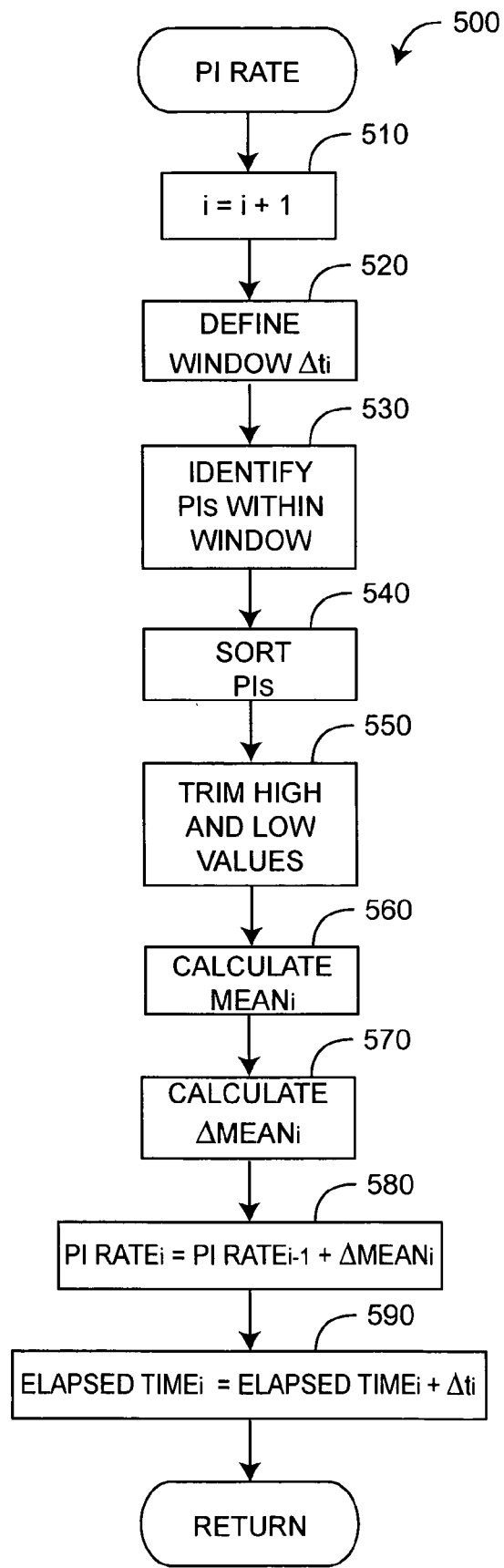
FIG. 5 is a flowchart for perfusion rate calculation.

FIG. 5 illustrates a PI rate calculation 500 embodiment. PI rate is calculated as a running sum of differential PI means ($\Delta mean_i$) between adjacent time windows $\Delta t_i$:

$$PI\ \text{rate} = \sum_{i=1}^{n} \Delta mean_i \quad (2)$$

$$\Delta mean_i = \text{mean}(PI)_{\Delta ti} - \text{mean}(PI)_{\Delta ti-1} \quad (3)$$

where mean $(PI)_{\Delta ti}$ is a trimmed mean of calculated PI values within window $\Delta t_i$. Calculated PI rate 500 begins by incrementing the integer index i 510 and defining a new window $\Delta t_i$ 520. PI values within the window $\Delta t_i$ are identified 530. The identified PI values are sorted according to value 540. A predetermined number of the highest and lowest PI values are deleted from the window 550. The mean value of the remaining PI values is calculated 560. The difference between the mean value corresponding to the present window and the mean value corresponding to the previous window is calculated 570, according to equation 3. This value is added to PI rate 580, which is the running sum of mean values according to equation 2. The elapsed time from the baseline is calculated 590, which is the running sum of $\Delta t_i$'s. In an embodiment, the trimmed mean is calculated by sorting the PI values in the time window from low to high, deleting a predetermined number of high and low values and calculating a mean for the remaining middle values. In an embodiment, each adjacent time window is of a 30 sec. duration and PI values are calculated every 1.2 sec. Thus, each 30 sec. time window has 25 PI values. In an embodiment, the trimmed mean deletes the 5 highest PI values and the 5 lowest PI values in the time window and calculates the mean of the middle 15 PI values. A monitor display 182 (FIG. 1) is selected that shows the PI rate 330 (FIG. 3) and that display is updated 440 (FIG. 4) with each calculated PI rate. In an embodiment, PI trend is the PI rate after a $\Delta T$ sec. interval from the baseline.

In an embodiment, PI values occurring during unstable data periods are deleted from the windows $\Delta t$ prior to mean calculations. In an embodiment, mean calculations require a minimum number of PI values. In an embodiment, PI data 320 (FIG. 3) is smoothed prior to or during PI rate and trend calculations, such as described in U.S. patent application Ser. No. 11/871,620, filed Oct. 12, 2007, entitled Perfusion Index Smoother, which is incorporated by reference herein.

Figure 6:
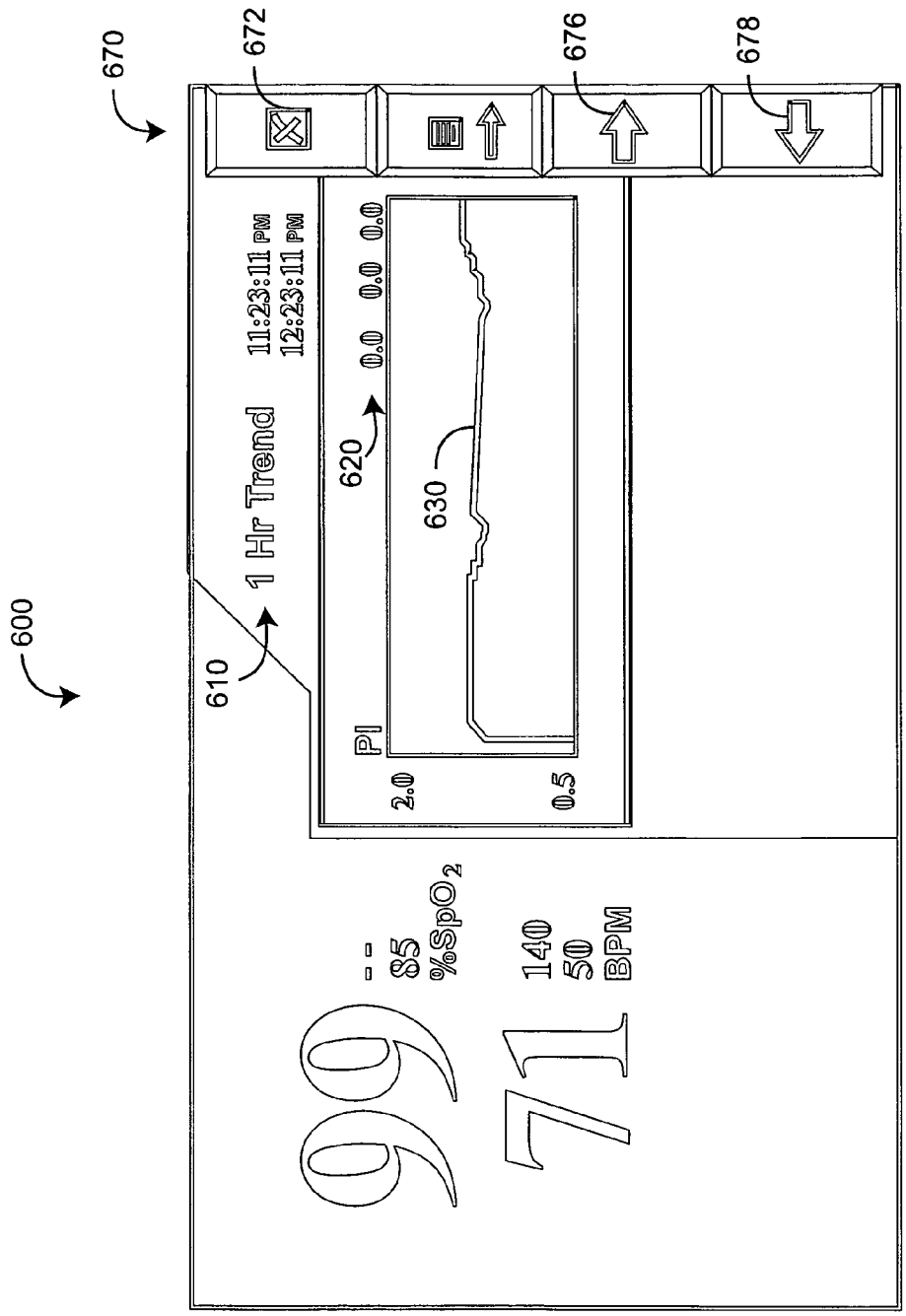
FIG. 6 is an illustration of a pop-up perfusion trend display.

FIG. 6 illustrates a trend view 600 having a time information area 610, a physiological measurement information area 320 and a PI trend graph 330. The time information area 310 on the trend view 300 shows the time scale of the trend graph, followed by the start time and end time of the data set that is displayed on the screen. The physiological measurement information area 320 of the trend view 300 shows the minimum, average, and maximum PI measurements contained in the displayed data set (excluding zero measurements). The PI trend graph 330 shows the perfusion index measurements displayed versus time. Depending on the trend period, a setting for how often the data is stored in the trend memory, the patient monitor 102 (FIG. 1) can store between 72 hours and 30 days worth of trend data. A PI trend display is described in U.S. patent application Ser. No. 11/904,046, filed Sep. 24, 2007, titled Patient Monitor User Interface, incorporated by reference herein.

As shown in FIG. 6, the trend view 600 also has soft key icon selections 370 including, for example, exit 372, next menu 374, scroll right 376 and scroll left 378 icons. Exit 372 is selected to return to the previous display view. Next menu 374 is selected to access the next page of menu selections. Scroll right 376 is selected to scroll through the data set in the forward time direction. Scroll left 378 is selected to scroll through the data set in the backward time direction. The display scrolls by ½ the selected time scale. For example, if a 2 hr display view is selected, then selecting scroll right 376 or scroll right 378 will scroll the displayed data by 1 hr to the left or right, respectively.

The soft key icon selections 370 may also include icons such as zoom, zoom from left, zoom from right, trend setup, histogram and clear trend data icons. Zoom is selected to change the time scale of the trend view. The available time scales are 24 hrs, 12 hrs, 8 hrs, 4 hrs, 2 hrs, 1 hr, 30 minutes, 10 minutes, 1 minute and 20 seconds. A trend view is described in U.S. patent application Ser. No. 11/904,046, filed Sep. 24, 2007, entitled Patient Monitor User Interface, which is incorporated by reference herein. In an embodiment, $\Delta PI$ 410 (FIG. 4) is set or reset by a clinician when a patient is initially hooked up. If the PI trend is less than $\Delta PI$, in addition to, or in lieu of, an alarm trigger, the trend view 600 pops-up on the patient monitor display. This pop-up perfusion trend display advantageously allows a doctor, clinician or other care provider to immediately verify a serious perfusion trend condition.

A perfusion trend indicator has been disclosed in detail in connection with various embodiments. These embodiments are disclosed by way of examples only and are not to limit the scope of the claims that follow. One of ordinary skill in art will appreciate many variations and modifications.

What is claimed is:

1. A perfusion trend indicator comprising:

an optical sensor that transmits multiple wavelengths of optical radiation into a tissue site, detects the optical radiation after attenuation by pulsatile blood flowing within the tissue site, and generates a sensor signal responsive to the detected optical radiation;

a patient monitor that demodulates the sensor signal so as to generate a plurality of plethysmograph channels;

a digital signal processor (DSP) within the patient monitor that inputs at least one of the plethysmograph channels and outputs a perfusion parameter accordingly;

a perfusion process that executes on the DSP so as to derive a perfusion trend from at least one of the plethysmograph channels, said perfusion trend different than historical values of said perfusion parameter, said perfusion trend responsive to trend values determined during relatively stable portions of said perfusion parameter, said trend values including at least a first baseline value during a first stable portion, a second value during a subsequent second stable portion, and a third value during a subsequent third stable portion, said perfusion trend responsive first to a first smoothed combination of said baseline and second values, and subsequently to a second smoothed combination of said second and third values, said stable portions including at least a plurality of values of said perfusion parameter; and a patient monitor output that is responsive to the perfusion trend.

2. The perfusion trend indicator according to claim 1 wherein the perfusion process comprises:

a plethysmograph input corresponding to the at least one plethysmograph channel having plethysmograph features; and a measure plethysmograph process that extracts a plurality of perfusion values from the plethysmograph according to the plethysmograph features.

3. The perfusion trend indicator according to claim 2 wherein the smoothing process further comprises an averaging process that generates a mean perfusion value of a set of perfusion values within a set time window.

4. The perfusion trend indicator according to claim 1 wherein the smoothing process further comprises a trim process that deletes outlying ones of the perfusion values within a time window according to predetermined criterion.

5. The perfusion trend indicator according to claim 4 wherein the patient monitor output a value representative of a sum of the first and second smoothed combinations.

6. The perfusion trend indicator according to claim 5 wherein the perfusion trend graph pops-up in a patient monitor display when the value representative of the first and second smoothed combinations after a predetermined time $\Delta T$ is less than a predetermined change in perfusion index $\Delta PI$.

7. A perfusion trend indicator, comprising:

a sensor that transmits multiple wavelengths of optical radiation into a tissue site and that detects the optical radiation after attenuation by pulsatile blood flow within a tissue site; and a digital signal processor (DSP) receiving as an input a plethysmograph responsive to said detected optical radiation, said DSP deriving perfusion index values responsive to said plethysmograph by generating perfusion index (PI) values from the plethysmograph according to predefined plethysmograph features and deriving a baseline PI value and PI trend values from the PI values relative to the baseline PI value, said PI trend values calculated by identifying stable data portions subsequent in time to the baseline PI value, smoothing said stable data portions and determining a difference between said smoothed stable data portions and said baseline PI; and outputting a value representative of said difference between said smoothed stable data portions and said baseline PI value.

8. The perfusion trend indicator according to claim 7, wherein said DSP calculates said PI trend values by identifying groups of PI values in a time window containing said stable data portions.

9. The perfusion trend indicator according to claim 8, wherein said DSP performs said smoothing on said groups of PI values by deleting outlying values from each of the identified groups of PI values.

10. The perfusion trend indicator according to claim 9, wherein said DSP performs said smoothing on said groups of PI values by averaging said groups of PI values.

11. The perfusion trend indicator according to claim 7 comprising a pop-up window that displays said value representing said difference between said smoothed stable data portions and said baseline PI value when said difference is less than a predetermined perfusion index $\Delta PI$ after a predetermined time $\Delta T$.

12. The perfusion trend indicator according to claim 7, wherein said DSP is positioned on a printed circuit board within a patient monitor.

* * * * *